United States Patent [19]

Kreh

[11] Patent Number: 4,794,172

[45] Date of Patent: Dec. 27, 1988

[54] CERIC OXIDANT

[75] Inventor: Robert P. Kreh, Jessup, Md.

[73] Assignee: W. R. Grace & Co.-Conn., New York, N.Y.

[21] Appl. No.: 917,462

[22] Filed: Oct. 10, 1986

[51] Int. Cl.[4] .............................. C07F 5/00; C25B 3/02
[52] U.S. Cl. .................................. 534/15; 204/78; 204/79
[58] Field of Search ...................... 534/15; 204/78, 79

[56] References Cited

U.S. PATENT DOCUMENTS

| | | | |
|---|---|---|---|
| 3,413,203 | 11/1968 | MacLean | 204/79 |
| 3,486,992 | 12/1969 | Frye | 204/86 |
| 4,482,438 | 11/1984 | Ballard et al. | 204/78 |
| 4,536,337 | 11/1985 | Komatsu et al. | 260/396 R |
| 4,639,298 | 1/1987 | Kreh et al. | 204/59 R |
| 4,647,349 | 3/1987 | Kreh et al. | 204/59 R |
| 4,670,108 | 6/1987 | Kreh et al. | 204/59 R |
| 4,701,245 | 10/1987 | Kreh | 204/78 |

FOREIGN PATENT DOCUMENTS 899856  5/1972  Canada .

OTHER PUBLICATIONS

J. Org. Chem. (1983) vol. 48, pp. 1487-1490 by M. Marrocco et al.

Prospects for the Indirect Electrolytic Oxidation of Organics by IBl et al., Electro-organic Synthesis Technology, No. 185, vol. 75 (1979) pp. 45-50.

*Primary Examiner*—John F. Terapane
*Assistant Examiner*—Virginia B. Caress
*Attorney, Agent, or Firm*—Howard J. Troffkin

[57] ABSTRACT

A solid product of the formula $Ce(CH_3SO_3)_2O.2H_2O$, $Ce(CH_3SO_3)_2(OH)_2.H_2O$ or other hydrates is disclosed and used as a highly effective oxidant to produce carbonyl containing products from aromatic and alkyl aromatic compounds.

9 Claims, 1 Drawing Sheet

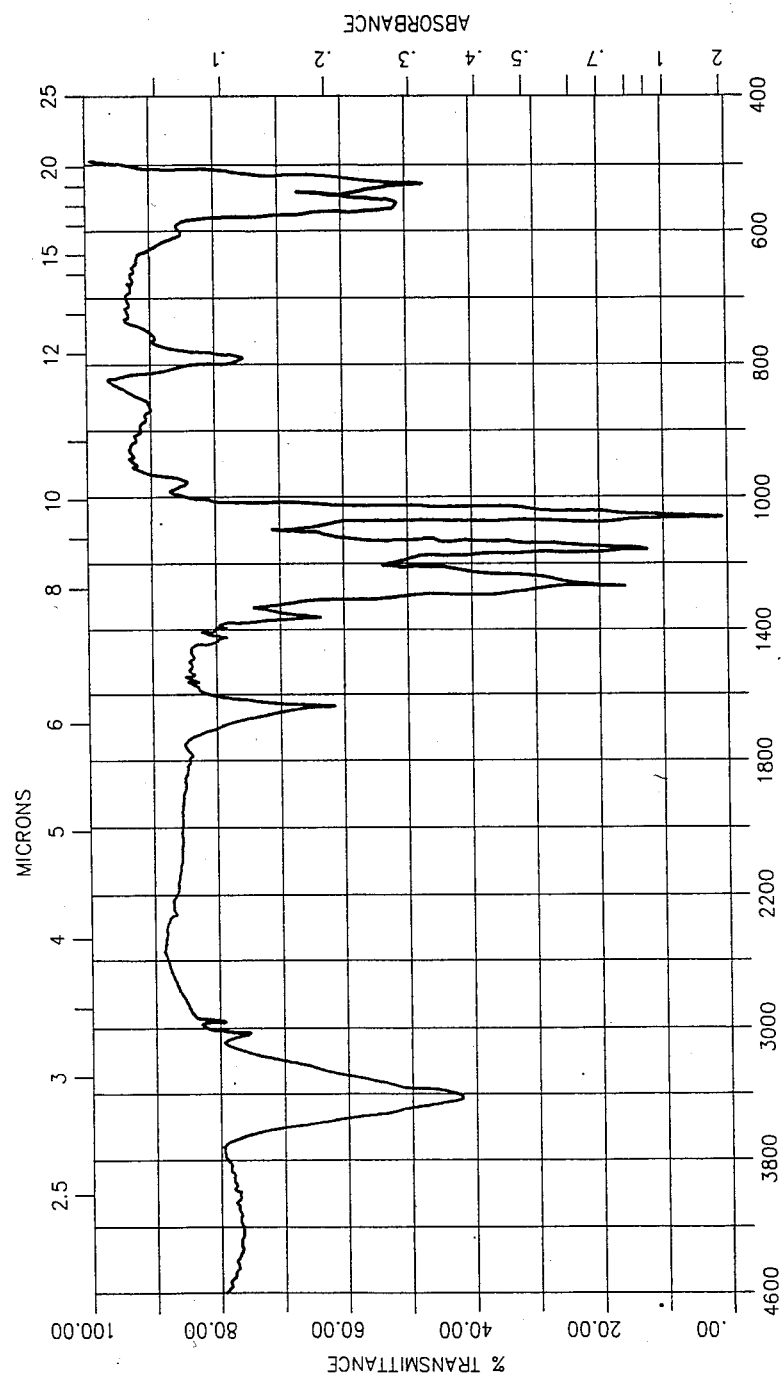

CERIC OXIDANT

The solid product, cerium(IV) methanesulfonate hydroxide hydrate, is disclosed and used in aqueous solutions as a highly effective oxidant to produce carbonyl containing products from aromatic and alkyl aromatic compounds.

BACKGROUND OF THE INVENTION

The present invention is directed to a novel, solid cerium(IV) product and to its utility as an oxidant of aromatic and alkyl substituted aromatic compounds to their corresponding carbonyl group containing compounds. More specifically the solid product described and claimed herein is a cerium methanesulfonate hydroxide hydrate.

Cerium(IV) is a well known oxidant for producing aromatic carbonyl compounds. However, none of the previously known cerium(IV) compounds is ideal for the purpose of achieving fast, selective oxidation of an aromatic compound. For example, anions of certain cerium salts (e.g., chloride, nitrate, perchlorate) are highly reactive with the organic substrate in a manner which cause the formation of large amounts of undesired by-products or exhibit unstable conditions which preclude their use on a commercial scale. Other less reactive anions (e.g., sulfates, acetate, fluoride, boron fluoride, silicon fluoride) generally form salts of low solubility, inhibit the rate of reaction and/or inhibit the ability of the spent oxidant to be readily regenerated. In addition, certain organic acid salts (e.g., benzenesulfonate) are insufficiently stable to be useful in the oxidation of organic compounds.

Although cerous/ceric ions have been known and used in oxidation reactions, there is a need to have a ceric oxidant which can be sufficiently stable under oxidizing conditions to be useful in indirect electrochemical processes, to be capable of undergoing repeated cycling between its cerous and ceric species under a high degree of efficiency, to be a highly selective oxidant in the formation of the desired carbonyl group containing compounds, to be capable of exhibiting high reaction rates to make the process in which they are used commercially attractive, to be a solid stable material capable of being easily transported, stored and metered in necessary quantities and to be capable of readily dissolving in water to provide an aqueous solution.

In a copending application, Ser. No. 859,548 filed May 5, 1986, now U.S. Pat. No. 4,639,298, applicant has described the use of an aqueous solution of cerium methanesulfonate in combination with at least 1.5 molar concentration of free methanesulfonic acid as an oxidation means to achieve high yield and selectivity in the formation of aromatic carbonyl containing compound. The solid ceric material presently described can be used for the same purpose to achieve the same result. It has the advantage of being a solid, easily transportable material which can be stored for extended periods prior to use. When use is desired it readily dissolves to form an oxidant solution.

SUMMARY OF THE INVENTION

The present ivvention is directed to a solid, stable product, ceric methanesulfonate hydroxide hydrate, as more fully described below, and to its use in an oxidation process to transform aromatic and alkyl substituted aromatic compounds to carbonyl containing compounds in high selectivity. The subject ceric oxidant has been found to exhibit the desired combination of properties (stability, solubility, reactivity, selectivity of carbonyl product formation, generation in high efficiency at high current density, and capability of repeated cycling between cerous and ceric specie) to provide a highly attractive product and process using same.

DETAILED DESCRIPTION OF THE INVENTION

The present invention is directed to an oxidant for selectively forming carbonyl containing compounds from respective aromatic compounds.

Certain terms used in the present specification and in the appended claims are defined hereinbelow to aid in providing a clear description of the invention:

The term "aromatic" shall, unless specifically indicated otherwise, refer to benzylic and fused benzylic compounds such as benzene, naphthalene, anthracene and the like. The compounds may be unsubstituted or may contain substitution groups which are inert to oxidation such as halides, alkoxy nitro, sulfonyl, amide, tertiary amino, tertiary alkyl and carboxylate groups.

The term "alkyl aromatic" refers to $C_1$-$C_6$ alkyl substituted benzylic and fused benzylic compounds. The compounds shall contain one or more than one primary or secondary $C_1$-$C_6$ alkyl group attached to the aromatic ring and may, in addition, contain groups which are inert to oxidation such as halides, alkoxy, nitro, sulfonyl, amido, tertiary amino, tertiary alkyl, and carboxylic groups. Examples of such compounds include toluene, (o, m or p) xylene, trimethylbenzene, (o, m or p) ethyltoluene, (o, m or p) propyltoluene, (o, m or p) methoxyethylbenzene, (o, m or p) ethoxyethylbenzene, 1, 2 dimethylnaphthalene, (o, m or p) methyl-N,N-dimethylaniline, (o, m or p) chlorotoluene and the like.

The term "indirect electrochemical oxidation" refers to an oxidation of an aromatic or alkyl aromatic compound which proceess in two steps such that the first step provides a metal ion oxidant (e.g. $Ce^{+4}$) by anodic charge exchange and the second step comprises the reacting of the metal ion oxidant with an aromatic or alkyl aromatic compound to produce carbonyl containing compounds. The oxidation of the aromatic or alkyl aromatic compound does not occur selectively in the absence of the metal ion oxidant. The indirect electrochemical oxidation of the organic substrate can be conducted in the electrochemical reactor (in-cell) or in a separate reactor (ex-cell).

The terms "cerous", "ceric" and "cerium" refer, respectively, to the cerium ion or salt of a cerium ion in its lower valence state (+3), its higher valence state (+4) and as a mixture of both lower and higher valence state species.

The ceric oxidant of the subject invention is a solid compound whihh shall be labeled ceric methanesulfonate hydroxide hydrate. The compound is represented by the atomic formula $CeC_2H_{10}S_2O_9$ which may translate into $Ce(CH_3SO_3)_2O.2H_2O$ or $Ce(CH_3SO_3)_2(OH)_2H_2O$. Additional water may be associated with the compound. The solid has an elemental analysis of 36.2 wt. % (theory 36.65 wt. %) cerium, 6.6 wt. % (6.3 wt. %) carbon, 17.0 wt. % (16.75 wt. %) sulfur, 2.6 wt. % (2.62 wt. %) hydrogen and 37.6 wt. % (37.7 wt. %) oxygen. The compound exhibits (via differential scanning calorimetry) the onset of the melting slope at 195.6° C. with a peak maximum at 215.5° C. Infrared spectral analysis (done with KBr pellet) of the subject compound is shown in FIG. 1.

The ceric methanesulfonate hydroxide hydrate of the present invention isaan excellent one-electron oxidant for organic compounds, in particular aromatic and alkyl substituted aromatic compounds. The subject compound can be used in a simple, one-step redox reaction or in a cyclical mediated process due to its ability to regenerate the oxidant specie. As discussed above and in applicant's copending U.S. patent application Ser. No. 859,548, certain cerium salts have anions which have detrimental effects, in either its oxidized or reduced form or in combination, on the reaction system. For example cerium sulfates and trifluoroacetates are known to have low solubility in weak acids and decreasing solubility with increased acid concentration.

The subject ceric compound of the present invention can be formed by contacting certain cerous salts with methanesulfonic acid to provide the cerous methanesulfonate intermediate, electrolytically oxidizing the intermediate in the presence of a small excess of free acid and recovering the resultant ceric methanesulfonate hydroxide hydrate. Specifically, the ceric compound is formed by contacting, in an aqueous solution, a cerous oxide, carbonate, hydroxide or mixtures thereof with a small excess of free methanesulfonic acid over that required to neutralize the initial cerous salt. Therefore, for each mole of aqueous salt (i.e., cerous carbonate, etc.) the solution should contain greater than three moles of free acid. The excess amount of acid should be small, such as from about 0.1 to 1.3 molar excess and preferably from about 0.5 to about 1.3 molar excess of free acid, over the stoichiometric amount required to form the cerous methanesulfonate. The concentration of cerous ions in the solution should be equal to or greater than about 0.2 molar and preferably from about 0.5 to 1.5 molar. Further, the solution should be free of extraneous anions of other inorganic acids such as sulfate, nitrate, perchlorate and the like. When such anions are present they should be removed by known means prior to using the solution to recover the subject compound. For example, if sulfate ions are present they can be removed by precipitation with lead(II) carbonate. Similarly, chloride ions can be removed by treating the solution with silver carbonate. Other extraneous ions can be removed in similar manners known in the art.

The solution so formed is introduced into an electrolytic cell which may be either undivided or preferably divided by a conventional porous partition wall or membrane between electrodes. The electrodes may be of any suitable form such as plates, lattices, expanded metal or reticulated porous material and the like. The anode may be of the known materials suitable for preforming the metal-ion oxidation and are, preferably selected from lead, lead hydroxide, platinum, platinized titanium, platinized niobium or metal hydroxide-titanium composite. The cathode of the cell may be any of the known materials suitable for performing reductions in the aqueous-acid solutions with or without the presence of metal ions such as, for example, steel, copper, and nickel. The cerous solution is introduced into the anolyte portion of a partitioned cell. The electrolytic cell provides an excellent means of permitting oxidation of cerous to ceric ions which combines with two moles of methanesulfonic acid to produce under the conditions described herein the present solid product, ceric methanesulfonate hydroxide hydrate. Further, the cerous solution has the ability to have a clean cathodic reduction without production of by-products which detract from the process and require separation therefrom.

The electrolysis can be performed at voltages ranging from about 2 to 20 volts with current density ranging between about 0.1 to about 500 mA/cm$^2$, preferably from 10 to 400 mA/cm$^2$ and most preferably from 30 to 300 mA/cm$^2$ (based on electrode area excluding roughness factor). The electrolysis may be conducted at a temperature of from about $-20°$ to $150°$ C. and preferably from $0°$ to $100°$ C.

The above described weakly acidic cerous methanesulfonate solution has, upon electrolysis oxidation, been found to yield a precipitate product of the desired ceric methanesulfonate hydroxide hydrate. The ceric compound can be readily recovered by filtration or the like and washing with water, acetonitrile or other non-solvent liquids.

The organic compounds which can be effectively oxidized using the present ceric compound are aromatic and alkyl aromatic compounds. The aromatic compounds include benzylic and fused benzylic ring compounds which may be unsubstituted or be substituted with a group which is substantially inert to oxidation. Examples of such compounds include benzene, naphthalene, anthracene and the like as well as such compounds which contain groups attached to the ring which are inert to the present indirect oxidation. Such groups can be readily determined by simple laboratory testing and include ($C_1$–$C_4$) alkoxy, tert-alkyl ($C_4$–$C_7$), phenoxy, nitro, tertiary amino, sulfonyl, amido, and carboxylate groups and the like. The alkyl substituted aromatic compounds include the above defined aromatic compounds which further contains at least one primary alkyl or secondary alkyl group or both.

Organic compounds, as described above, can be oxidized to their respective carbonyl compounds by contacting the organic compound with a solution or suspension containing the subject ceric methanesulfonate hydroxide hydrate. Suspensions or dispersions of the subject ceric methanesulfonate hydroxide hydrate useful as an oxidizing means can be readily formed by using the initially formed weakly acidic system having the solid ceric salt therein or dispersing the solid ceric salt in a weakly acidic aqueous system. Solutions of the ceric compound can be formed by dissolving the compound in water. Although the subject compound is substantially insoluble in weakly acidic aqueous solutions (such as solutions having from 0.1 to 1.3 molar concentration of methanesulfonic acid), it has been surprisingly found that the compound is very highly soluble in substantially neutral (pH 6.5–7.5) or D.I. water. Thus, aqueous solutions of the ceric methanesulfonate hydroxide hydrate can be readily formed by dissolving the subject ceric compound in plain water. Oxidation of organic compounds can be carried out in strong acidic solutions, that is, solutions having a concentration of at least 1.5 molar free methanesulfonic acid. These solutions can be formed be rapidly adding the necessary amount of acid to the ceric compound-water solution to provide the required at least 1.5 molar acid concentration.

The ceric oxidant can be contacted with an aromatic or alkyl aromatic compound merely by dissolving or dispersing the compound in the aqueous system containing the ceric oxidant. The aromatic or alkyl aromatic compound can be introduced to the reactor either dissolved or dispersed in the aqueous phase or dissolved in an organic solvent.

The ceric oxidant and aromatic or alkyl aromatic compound can be contacted in a batch manner. Preferably, the oxidant can be used in a continuous mediated process in which the aromatic or alkyl aromatic compound and ceric oxidant are contacted in a reaction vessel under agitation. The compound and oxidant are continuously introduced into the reaction vessel. The solution containing spent (cerous) oxidant and the resultant carbonyl containing aromatic or alkyl aromatic compound is removed and the carbonyl compound recovered by conventional means, such as distillation, phase separation, precipitation or extraction with an appropriate solvent such as dichloroalkanes, cyclohexane and the like. The particular mode of separation will depend upon the identity of the product formed and can be readily ascertained by the artisan. The remaining solution can then be transferred to an electrochemical cell where the aqueoss acidic medium rich in cerous ions is electrolytically regenerated to a ceric rich system. The oxidation system should contain cerium ions in at least 0.2 molar and preferably at least 0.5 molar concentration.

The above described process (in particular the mediated process) using the subject oxidant as the starting source of ceric oxidant is capable of providing ceric ions in high concentration to provide high reaction rates in oxidizing the organic compound. In addition, the process unexpectedly provides a means for readily and selectively forming quinones (from aromatic compounds) and aldehydes or ketones (from alkyl aromatics) without substantial by-product formation.

The organic oxidation can be carried out under ambient temperature and pressure conditions. The temperature may be varied from about 0° to about 100° C. with from 20° to 75° C. being preferred. The pressure may be elevated or reduced for process reasons.

The following examples are given for illustrative purposes only and are not meant to be a limitation on the present invention as defined by the claims appended hereto. All parts and percentages are by weight unless otherwise indicated.

EXAMPLE I 276 parts of methanesulfonic acid were added slowly to a stirred suspension of 219 parts of cerium carbonate (obtained as the pentahydrate) in 150 parts water. Upon completion of the evolution of carbon dioxide, water was added to make the volume 450 milliliters, containing 1.8M cerous methanesulfonate [$Ce(CH_3SO)$] and 1M of free methane sulfonic acid.

The above solution was introduced into the anolyte compartment of a plate-and-frame type electrolytic cell. The anode was a platinum-clad niobium sheet having the surface coated with 63.5 micrometers of platinum (total surface area ca. 50 cm²) The anolyte was separated from the catholyte compartment by a commercial perfluorinated polyolefin ion exchange membrane (Nafion 390). The anolyte temperature was ca. 40° C., and a constant current of 5 amps was passed for 54 min., followed by 3 amps for 211 min. A slurry resulted in the anolyte compartment. The slurry had a total cerium-(IV) content of 0.53 mole (theoretical yield is 0.56; 94.6% current efficiency). The catholyte compartment contained a stainless steel cathode and caused a clean proton reduction to hydrogen gas.

The anolyte slurry was stirred overnight at ambient temperature. The solid product was separated by filtration and dried for about 15 hours at 60° C. under vacuum. The recovered product was washed with 150 ml of acetonitrile and then again dried under vacuum at 60° C. for about 15 hours yielding 97.3 parts of yellow solid. This yellow solid had the following elemental analysis, in agreement with $Ce(CH_3SO_3)_2(OH)_2 \cdot H_2O$. Calculated: Ce, 36.65%; C, 6.28%; S, 16.75%; H, 2.62%; Found: Ce, 36.2%; C, 6.59%; S, 16.97%, H, 2.57%. Differential scanning calorimetry showed the onset of the melting slope at 195.6° C. with a peak maximum of 215.5° C. The infrared spectrum (KBr pellet) is shown in FIG. 1.

EXAMPLE II 23 parts of $Ce(CH_3SO_3)_2(OH)_2 \cdot H_2O$ were introduced into 120 parts of water, and stirred to dissolve the solid. The solution was then heated to 60° C. 30 parts by volume of methanesulfonic acid were added dropwise over approximately 15 seconds. The solution was purged with nitrogen and a solution of 1.28 parts of naphthalene in 30 parts by volume of 1,2-dichloroethane was added. After stirring vigorously for 45 minutes the resulting mixture was cooled and extracted with 300 parts methylene chloride. Quantitative analysis by gas chromatography showed a 90 percent conversion of naphthalene and 90% selectivity to 1,4-naphthoquinone.

EXAMPLE III 23 parts of $Ce(CH_3SO_3)_2O \cdot 2H_2O$ were introduced into 140 parts of water, and the mixture was stirred for five minutes to dissolve the solid. The solution was then heated to 60°. 65 parts by volume of methansulfonic acid were added dropwise over approximately 45 seconds. The resulting solution was purged with nitrogen, and then 2.0 parts of p-xylene was added. After stirring vigorously for 30 minutes, the resulting mixture was extracted with 300 parts methylene chloride. Quantitative analysis by gas chromatography showed a 90% conversion of p-xylene and 86% selectivity to p-tolualdehyde.

I claim:

1. A Solid product having of having a formula selected from $Ce(CH_3SO_3)_2 \cdot OxH_2O$ and $Ce(CH_3SO_3)_2(OH)_2 \cdot xH_2O$ wherein x is an integer equal to or greater than 1.

2. The product of claim 1 wherein the product has the atomic formula $CeC_2H_{10}S_2O_9$ and the structural formula selected from $Ce(CH_3SO_3)_2O \cdot 2H_2O$ or $Ce(CH_3SO_3)_2(OH)_2 \cdot H_2O$.

3. The product of claim 2 wherein the structural formula is $Ce(CH_3SO_3)_2O \cdot 2H_2O$.

4. The product of claim 2 wherein the structural formula is $Ce(CH_3SO_3)_2(OH)_2 \cdot H_2O$.

5. The product of claim 1 wherein the product is capable of exhibiting an infrared spectrum containing three strong intensity peaks at 1060, 1150 and 1260 $cm^{-1}$ and five moderate intensity peaks at 520, 560, 780, 1350 and 1630 $cm^{-1}$.

6. The product of claim 2 wherein the product is capable of exhibiting an infrared spectrum containing the strong intensity peaks at 1060, 1150 and 1260 $cm^{-1}$ and five moderate intensity peaks at 520, 560, 780, 1350 and 1630 $cm^{-1}$.

7. The product of claim 3 wherein the product is capable of exhibiting an infrared spectrum containing three strong intensity peaks at 1060, 1150 and 1260 cm$^{-1}$ and five moderate intensity peaks at 520, 560, 780, 1350 and 1630 cm$^{-1}$.

8. The product of claim 4 wherein the product is capable of exhibiting an infrared spectrum containing three strong intensity peaks at 1060, 1150 and 1260 cm$^{-1}$ and five moderate intensity peaks at 520, 560, 780, 1350 and 1630 cm$^{-1}$.

9. A product comprising ceric methanesulfonate hydroxide hydrate formed by contacting, in an aqueous medium, a cerous salt selected from cerous oxide, cerous carbonate, cerous hydroxide or mixtures thereof with from 0.1 to 1.3 molar excess of methanesulfonic acid sufficient to form cerous methanesulfonate and said cerous cations are present in at least 0.2 molar concentration; electrolytically oxidizing the cerous ions to ceric ions; and separating the solid ceric methanesulfonate hydroxide hydrate from the aqueous medium.

* * * * *